United States Patent
Maruyama

(10) Patent No.: US 8,775,098 B2
(45) Date of Patent: Jul. 8, 2014

(54) PREPARATIVE LIQUID CHROMATOGRAPH SYSTEM

(75) Inventor: Shuzo Maruyama, Kameoka (JP)

(73) Assignee: Shimadzu Corporation, Kyoto-Shi (JP)

( * ) Notice: Subject to any disclaimer, the term of this patent is extended or adjusted under 35 U.S.C. 154(b) by 139 days.

(21) Appl. No.: 13/059,222

(22) PCT Filed: Aug. 19, 2008

(86) PCT No.: PCT/JP2008/002231
§ 371 (c)(1), (2), (4) Date: Mar. 29, 2011

(87) PCT Pub. No.: WO2010/021008
PCT Pub. Date: Feb. 25, 2010

(65) Prior Publication Data
US 2011/0184658 A1 Jul. 28, 2011

(51) Int. Cl.
*G06F 19/00* (2011.01)
*G01N 30/06* (2006.01)

(52) U.S. Cl.
USPC .............................................. 702/25; 422/70

(58) Field of Classification Search
CPC ............... B01D 15/247; B01D 15/325; B01D 15/3804; B01D 15/22; G01N 30/02; G06F 19/00; G06F 19/10; G06F 19/12; G06F 19/22
USPC .............................................. 702/25; 422/70
See application file for complete search history.

(56) References Cited

U.S. PATENT DOCUMENTS 5,100,557 A * 3/1992 Nogami et al. ............... 210/656
6,767,467 B2   7/2004 Fischer et al. ................ 210/659
7,086,279 B2   8/2006 Gilby et al. .................... 73/61.57
2002/0121468 A1   9/2002 Fischer et al. ............. 210/198.2

(Continued)

FOREIGN PATENT DOCUMENTS

JP  2004-101198  4/2004
JP  2007-183173  7/2007

OTHER PUBLICATIONS

G. Rigaut, et al., "A genetic protein purification method for protein complex characterization and proteome exploration", 1999 Nature America Inc.*

(Continued)

*Primary Examiner* — John Breene
*Assistant Examiner* — Ruihua Zhang
(74) *Attorney, Agent, or Firm* — Bingham McCutchen LLP

(57) ABSTRACT

A sample is introduced from an injector unit into a mobile phase. One target component is separated into a plurality of vials by a fraction collector. Next, a sampler sequentially suctions the eluate from the plurality of the vials and performs an LC analysis on each of the eluate portions, thereby producing a chromatogram. A peak detector calculates the peak area corresponding to the amount of the target component in each chromatogram. A delay estimator extracts the peak area in the fraction having the maximum peak area and the peak areas in the previous and succeeding fractions on the time axis of the foregoing fraction. Then, the delay estimator estimates a delay volume from a detector to the tip end of the dispenser nozzle based on data such as the peak areas, the flow rate of the liquid fed from the pump, positions of the vials, and the position of the peak of the target component in the chromatogram detected by the detector, and stores the delay volume. Upon preparative separation of a desired component, a delay time is calculated based on the delay volume and the flow rate and the timing for the preparative separation is controlled based on the delay time.

16 Claims, 3 Drawing Sheets

(56) References Cited

U.S. PATENT DOCUMENTS

2004/0018118 A1\* 1/2004 Waki ............................... 422/70
2004/0216510 A1 11/2004 Gilby et al. .................... 73/1.42
2006/0075806 A1 4/2006 Gilby et al. ................... 73/61.57
2006/0101898 A1\* 5/2006 Umemura ..................... 73/23.37

OTHER PUBLICATIONS

Japanese language international preliminary report on patentability dated Mar. 8, 2011 and its English language translation for corresponding PCT application PCT/JP2008/002231.

Chinese language office action dated Nov. 5, 2012 and its English language translation issued in corresponding Chinese application 200880130804.6.

Chinese Office Action dated Apr. 17, 2013 for corresponding Chinese Patent Application No. 200880130804.6, English translation of "Reason for Rejection".

Chinese Office Action dated Nov. 7, 2013 for corresponding Chinese Patent Application No. 200880130804.6, English translation of "Reason for Rejection" (11 pages).

\* cited by examiner (a) FRACTIONATION/PREPARATIVE SEPARATION (b) RESULT OF PREPARATIVE SEPARATION (c) RESULT OF INDIVIDUAL LC ANALYSIS (CHROMATOGRAMS)

US 8,775,098 B2

PREPARATIVE LIQUID CHROMATOGRAPH SYSTEM

CROSS-REFERENCE TO THE RELATED APPLICATIONS

This application is a national stage of international application No. PCT/JP2008/002231, filed on Aug. 19, 2008, the entire contents of which are incorporated herein by reference.

TECHNICAL FIELD

The present invention relates to a preparative liquid chromatograph system which fractionates an eluate containing a component isolated in a column, and collects the eluate separately in a plurality of containers.

BACKGROUND ART

Preparative liquid chromatograph systems (hereinafter referred to as a preparative LC system) have been known as systems which fractionate and collect a plurality of components contained in a liquid sample by use of a high-performance liquid chromatography (HPLC). A preparative LC system detects a sample component in an eluate when the eluate passes through a detector such as an ultraviolet-visible light absorption detector and controls preparative separation of the eluate in a fraction collector at a timing based on the detected signals. It generally takes a certain amount of time before the eluate arrives at a dispenser nozzle after passing through the detector. The delay time depends on the volume of flow channels from the detector to a tip end of the dispenser nozzle (hereinafter referred to as a delay volume), and flowing amount (flow rate) of a mobile phase. Therefore, in order to achieve accurate starting and ending of preparative separation of the target component in the fraction collector, it is necessary to precisely know the delay time, and is thus necessary to precisely obtain the delay volume.

A conventionally known preparative LC apparatus includes a means for allowing users to estimate the delay volume based on the inner diameter and the length of flow channels from an exit of a detector to the tip end of a dispenser nozzle, and to input numerical values of the delay volume. However, since such estimation sometimes includes errors, it is difficult to obtain the delay volume with high accuracy. Furthermore, an erroneous delay volume may be set due to human errors such as miscalculation by the user. Accordingly, it has been problematically difficult to accurately separate the component corresponding to a desired peak that appears in a chromatogram.

According to the preparative LC apparatus disclosed in Patent Document 1, a detector is provided on both the upstream and downstream sides of a fraction collector. Delay time in detecting the same component in the eluate between the two detectors is measured, and a delay volume is estimated based on the delay time. However, this method does not consider inner volumes of portions which are not included in the flow channel between the two detectors, such as channel-changing valves and dispenser nozzles, and thus problematically the calculated delay volume may not be sufficiently accurate. Further, disposing two detectors respectively on both the upstream and downstream sides of the fraction collector poses a problem of a complex structure.

The preparative LC apparatus disclosed in Patent Document 2 has a structure in which part of an eluent is branched through a splitter and a detector is provided. In the structure, another detector is positioned just prior to the fraction collector, and the delay time for a predetermined component in an eluate is measured using the detection results from the detector. Then, the delay volume is estimated from the delay time. However, similarly with the foregoing prior art, this method does not consider the volumes of a flow changing valve and a dispenser nozzle inside the fraction collector. Further, addition of another detector only for measuring the delay time leads to an increase in the production cost.

[Patent Document 1] U.S. Pat. No. 7,086,279
[Patent Document 2] U.S. Pat. No. 6,767,467

DISCLOSURE OF THE INVENTION

Problems to be Solved by the Invention

The present invention has been achieved to solve the aforementioned problems, and the main objective thereof is to provide a preparative liquid chromatograph system which can accurately obtain the delay time of an eluate required for controlling the timing for preparative separation and thus can properly separate and collect the target component. Another objective of the present invention is to provide a preparative liquid chromatogram system which does not need a dedicated detector for estimating the delay time and thus can reduce the production cost.

Means for Solving the Problem

The present invention created to solve the problems is a preparative liquid chromatogram apparatus having an LC unit including a column for isolating a component in a sample and a detector for detecting the component in an eluate from the column, and a fraction collector for fractionating the eluate and separating each fraction of the eluate in individual containers, wherein the preparative liquid chromatograph system includes:

a) a preparative separation execution controller for controlling the LC unit and the fraction collector to separate a target component in a predetermined sample into a plurality of individual containers per a predetermined fractionation time;

b) an individual LC execution controller for controlling the LC unit to perform an LC analysis individually on the target component separated in the plurality of containers;

c) a peak data calculator for calculating a peak data corresponding to the amount of the target component in a chromatogram obtained as a result of the LC analysis performed by the individual LC execution controller; and d) a calculation processor for estimating delay data on a delay occurring in a period from detection of a component in the eluate with the detector to preparative separation of the component with the fraction collector, by using at least the peak data corresponding to the maximum amount and its previous and succeeding peak data on the time axis obtained by the peak data calculator.

As the target component in the predetermined sample, components whose retention time is known are selected. Specifically, standard samples (samples for test) containing a known component are preferably used as the predetermined sample.

When the sample is introduced into a column, the component in the sample spreads to some extent over time. Accordingly, when the component is separated in a plurality of containers at a fractionation time width which are sufficiently smaller than the time width (time between start and end of the peak) of the component's peak in the chromatogram, the amount (concentration) of the target component in the eluate separated in each of the plurality of containers stepwise increases with time and thereafter stepwise decreases. Given that a chromatogram at a tip end of the dispenser nozzle of the fraction collector is produced, the amount of the component in the eluate becomes greatest (maximum amount) in the container corresponding to the fraction which includes a peak top in the chromatogram. The amount of the component is smaller than the maximum amount in the eluate in the containers corresponding to the previous and succeeding fractions on the time axis of the fraction giving the maximum amount. For example, in the case where the amount of the component is identical in the eluate in the containers corresponding to the previous and succeeding fractions on the time axis of the fraction giving the maximum amount, it can be assumed that a peak top exists in the middle of the time period of the fraction giving the maximum amount. Moreover, based at least on the ratio of the amount of the component in the eluate between the containers corresponding to the previous and succeeding fractions on the time axis, it is possible to estimate the position of the peak top in the time period of the fraction giving the maximum amount.

Therefore, according to the preparative liquid chromatogram system of the present example, a target component in a predetermined sample is separated in a plurality of containers under the control of the preparative separation execution controller. For measuring the amount of the target component in the separated eluate in each container, the eluate collected in each container is LC analyzed, and a chromatogram is produced so that a peak data of the target component are obtained. The peak height may be used as the peak data, and preferably the peak area is used. The calculation processor uses at least the peak data corresponding to the maximum amount and its previous and succeeding peak data on the time axis so as to estimate delay data on the delay occurring in the period from detection of a component in the eluate to preparative separation of the component with the fraction collector.

As a concrete embodiment, the calculation processor may estimate the delay volume of the eluate flowing in the period from detection of a component in the eluate with the detector to preparative separation of the component with the fraction collector, based on the plurality of the peak data, an amount of mobile phase flowing during the preparative separation conducted by the preparative separation execution controller, a peak position of the target component in the chromatogram during the preparative separation, and a position of the container at which the peak data corresponding to the maximum amount is obtained or time data of when the preparative separation to this container is executed. Further, the delay time in the period from detection of a component in the eluate with the detector to preparative separation of the component with the fraction collector is obtainable based on the delay volume and the flow amount (flow rate) of the mobile phase.

The thus estimated delay volume and the delay time reflect, for example, all flow channels from an exit of the detector (or component detection position in a flow cell in the detector) to a tip end of the dispenser nozzle of the fraction collector, and thus inner volumes of the channel-changing valves and nozzles in the fraction collector are considered. For this reason, it is possible to obtain the delay volume and the delay time with sufficiently high accuracy as compared with various known methods.

The preparative liquid chromatograph system according to the present invention may have a structure in which the calculation processor stores the estimated delay data, and the preparative separation execution controller controls, upon preparative separation of a given component in the sample, the timing of preparative separation of the component by using the delay data.

This structure makes it possible to determine the timing for preparative separation of the desired component by using the delay data which has been accurately obtained as mentioned earlier. Therefore, it is possible to assuredly separate and collect the desired component, or in other words, without leakage and including a minimum amount of undesired components.

Effects of the Invention

As compared with conventional products, the preparative liquid chromatograph system according to the present invention can more accurately obtain delay time occurring in the period from detection of a component in an eluate with a detector to preparative separation with a fraction collector, or delay volume which expresses the delay time by volumes of the channel route. It is thus possible to improve the accuracy in preparative separation of the desired component. Moreover, it is also possible to obtain the delay data solely by utilizing a detector which is used for normal preparative separation or LC analysis. Accordingly, since addition of another detector is not necessary, cost for the system can be saved.

If the preparative liquid chromatograph system according to the present invention is provided with a sample introduction means (auto sampler) for automatically selecting each portion of the eluate separated in the plurality of containers and for sequentially subjecting the selected portion of the eluate to an LC analysis, a series of operations for calculating the delay data can be almost fully automated without any manual operation.

EXPLANATION OF NUMERALS

1 . . . Mobile Phase Container
2 . . . Liquid Feed Pump
3 . . . Injector Unit
31 . . . High Pressure Valve
32 . . . Sample Loop
33 . . . Measuring Unit
34 . . . Sampler
35 . . . Actuator
4 . . . Column
5 . . . Detector
6 . . . Fraction collector
61 . . . Nozzle Head
62 . . . Dispenser Valve
63 . . . Dispenser Nozzle
64 . . . Waste Vessel
65 . . . Actuator
66 . . . Rack
67 . . . Vial
7 . . . Data Processor 71 . . . Chromatogram Producing Section
72 . . . Peak Detector
73 . . . Delay Estimator
8 . . . Controller
9 . . . Personal Computer
10 . . . Input Unit
11 . . . Display

BEST MODE FOR CARRYING OUT THE INVENTION

Figure 1:
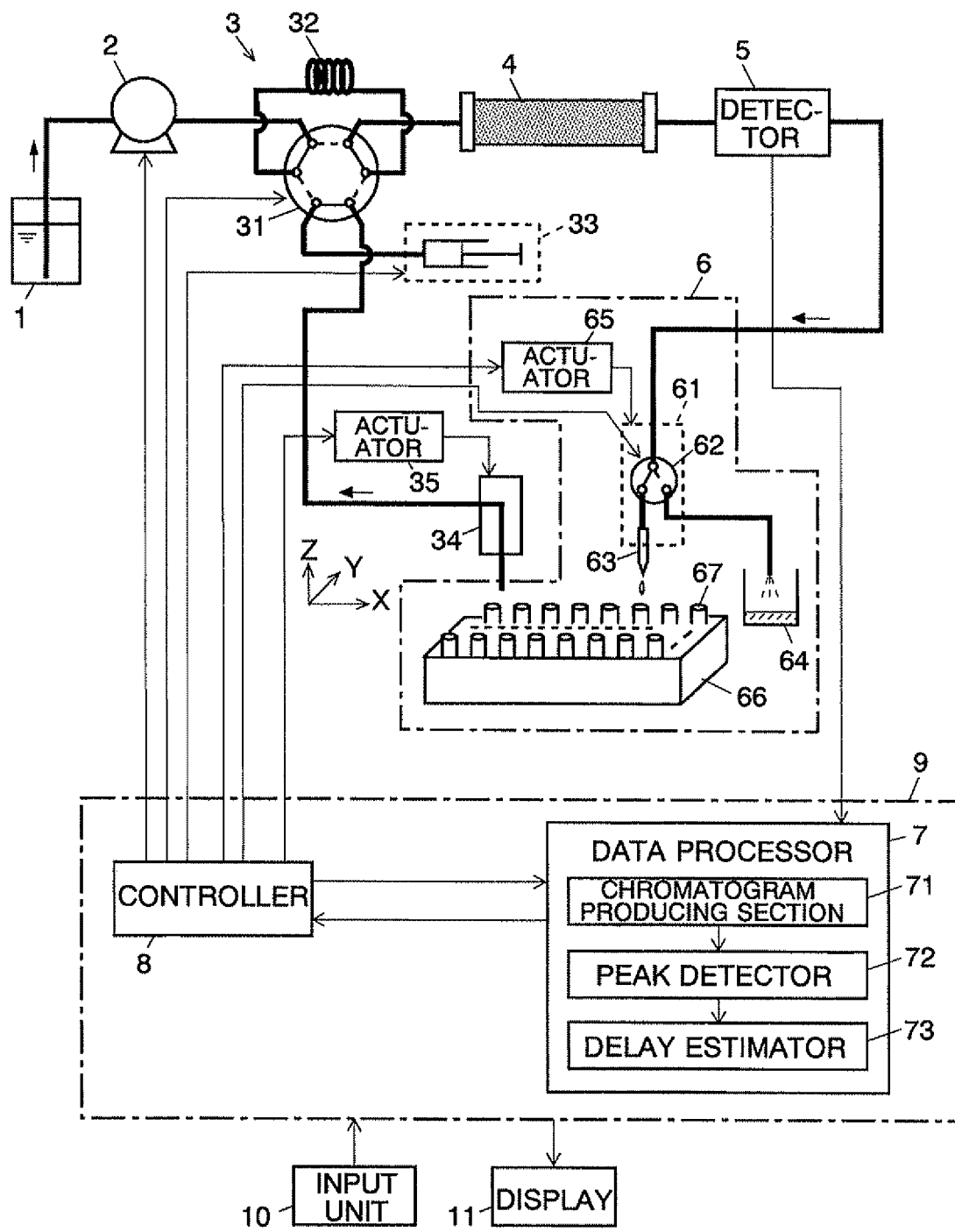
FIG. 1 is a configuration diagram showing the main parts of the preparative LC system according to one embodiment of the present invention.

The following description will discuss a preparative liquid chromatograph system (hereinafter, referred to as a preparative LC system) according to one embodiment of the present invention with reference to the attached figures. FIG. 1 is a configuration diagram showing the main parts of the preparative LC system according to the present embodiment.

In the preparative LC system, a liquid feed pump 2 suctions a mobile phase stored in a mobile phase container 1 and supplies it through an injector unit 3 into a column 4 at a constant flow rate. The injector unit 3 includes a 6-port, 2-position (flow channels indicated by solid lines and flow channels indicated by dotted lines shown in FIG. 1) high pressure valve 31, a sample loop 32, a measuring unit 33 having a measuring syringe, a sampler 34, an actuator 35 which moves the sampler 34 in three axis directions of X, Y and Z shown in FIG. 1, and other members. The injector unit 3 injects a predetermined amount of a sample liquid having been suctioned by the sampler 34 from a vial 67, which is to be explained later, into the mobile phase at a predetermined timing. In the injector unit 3, upon injection of the sample liquid into the mobile phase, the flow of the mobile phase conveys the sample liquid into the column 4. While passing through the column 4, the sample liquid is separated into various components along the time axis and then eluted. The eluate from the column 4 is introduced through a detector 5 to a fraction collector 6.

The fraction collector 6 includes a nozzle head 61 with a built-in dispenser valve 62 for switching the flow of the eluate, which has passed through the detector 5, to either of two flow channels of a dispenser channel and a drain channel, a dispenser nozzle 63 installed at an end of the dispenser channel, a rack 66 housing a large number of the vials 67, an actuator 65 which moves the nozzle head 61 in three axis directions of X, Y and Z shown in FIG. 1, and a waste vessel 64 which collects the eluate discharged from the end of the drain channel. In the fraction collector 6, the actuator 65 appropriately moves the nozzle head 61 in response to directions from a controller 8 so as to dispense the eluate into any of the vials 67 or to discharge unnecessary eluates into the waste vessel 64.

The preparative LC system according to this embodiment has a structure in which the sampler 34 in the aforementioned injector unit 3 can directly suction the sample liquid from any of the large number of the vials 67 in the fraction collector 6. The structure is not limited to the one shown in FIG. 1 as long as the sampler 34 can directly suction the sample liquid dispensed in the vial 67 in the fraction collector 6. For example, the structure may be such that a carrier such as a robot arm takes a predetermined vial 67 out of the rack 66 and delivers it to the location of the sampler 34 so that the sampler 34 suctions the sample liquid in the delivered vial 67.

The detector 5 may be, for example, an ultraviolet-visible light absorption detector, a photodiode array detector, a deferential refractive index detector, or other types of detectors, and includes a flow cell through which the eluate passed. The detector 5 outputs detection signals in accordance with the amount (concentration) of a sample component in the eluate passing through the flow cell. The detection signals are converted to digital data by an analog-to-digital (A/D) converter installed in the detectors and are then inputted in a data processor 7 which performs predetermined data processing. The data processor 7 has a chromatogram producing section 71, a peak detector 72, a delay estimator 73, and other members as function blocks to execute a processing operation specific to the present invention, which will be described later. The controller 8 controls each of the liquid feed pump 2, the high pressure valve 31, the measuring unit 33, the actuators 35 and 65 to perform an LC analysis and preparative separation/fractionation operations and others.

The data processor 7 and the controller 8 can normally be embodied centering on a personal computer 9. Activation of a predetermined controlling/processing software program installed in the personal computer 9 can execute the functions of the data processor 7 and the controller 8. The personal computer 9 is connected to an input unit 10 by which a user specifies LC analysis conditions or preparative separation/fractionation conditions, and to a display 11 for displaying results of the analysis (e.g. chromatogram).

Figure 2:
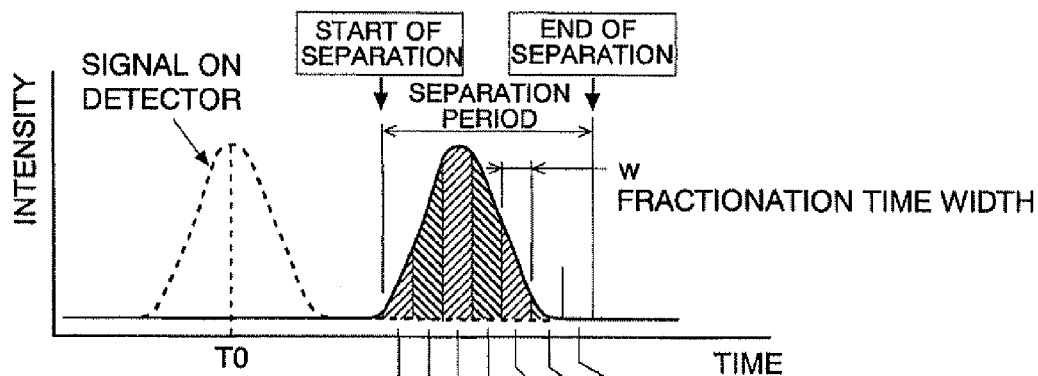
FIG. 2 is an explanatory diagram showing delay data acquisition process in the preparative LC system according to the present embodiment.
Figure 2:
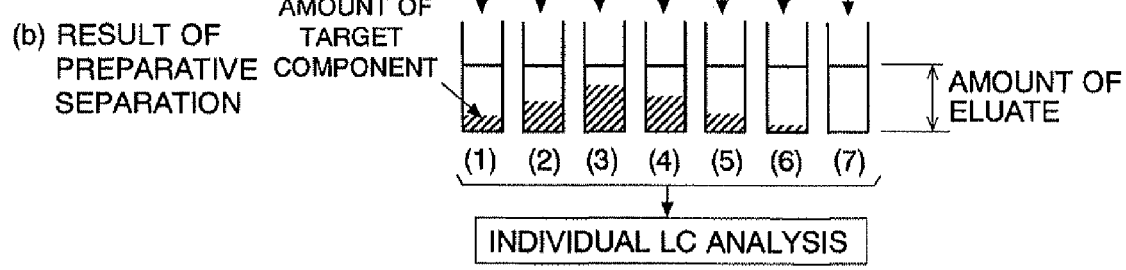
Figure 2:
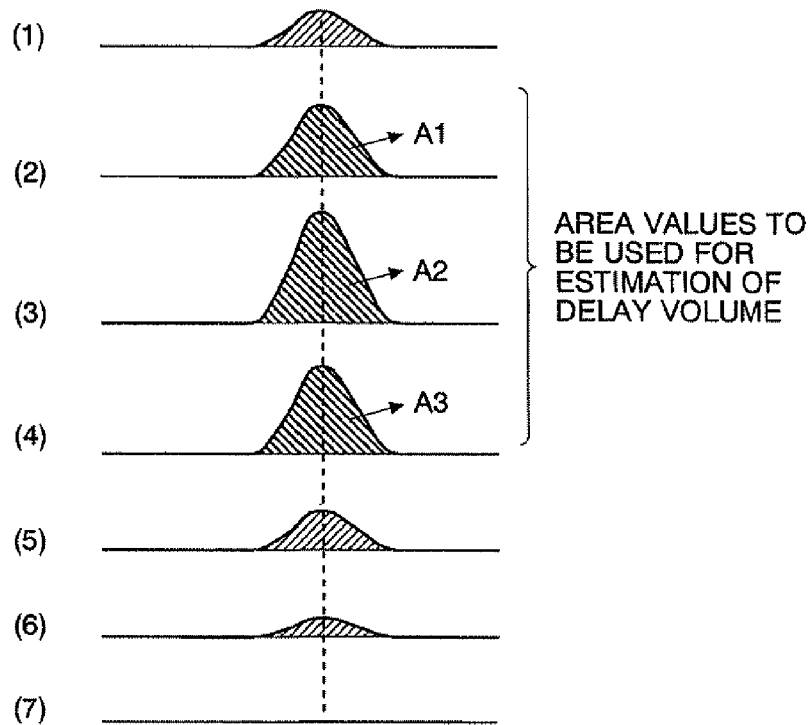

The following description will discuss the delay data acquisition operation which is the specific processing operation according to the preparative CL system of the present embodiment with reference to FIG. 2. The "delay data" used herein refers to volume (delay volume) of the flow channel between an exit of the detector 5 (or location immediate posterior to the detection position of flow cell inside the detector 5) and a tip end of the dispenser nozzle 63 in the fraction collector 6 in FIG. 1, or time (delay time) required for a component in the mobile phase to reach a tip end of the dispenser nozzle 63 in the fraction collector 6 after passing through the detector 5 (precisely, the detection position of the flow cell inside the detector 5). The delay time is determined based on the delay volume and a feed rate of the liquid feed pump 2. The delay data acquisition operation may be performed, for example, as one of the calibration procedures of the preparative LC system.

For performing the delay data acquisition operation, a user prepares a standard sample containing a known target component in a predetermined vial. The target component is a component whose retention time under a predetermined feed rate of the pump is known. The user previously obtains an approximate delay time using results of a rough calculation of the delay volume under the same feed rate of the pump so as to determine a period for separating the target component in the standard sample based on the retention time and the approximate delay time of the target component. The period is set from the input unit 10 as one of the conditions for the preparative separation/fractionation. Even if the approximate delay time is unclear, it is possible to assuredly separate the target component by, for example, starting the preparative separation immediately after detection of the target component by the detector 5 (though this method is inefficient in that the eluate not containing the target component is also separated and collected in many vials). Therefore, it is not always necessary to determine the approximate delay time and use it to set the preparative separation period.

In this example, a preparative separation period is set as shown in FIG. 2(a). Preparative separation/fractionation conditions during the preparative separation period are set in a manner that time-series fractionation is performed at a predetermined fractionation time width w so that each fraction of the eluate is separated in an individual vial. It is essential that the fractionation time width w be sufficiently narrower than the width of the peak time of the target component appearing in the chromatogram. Further, it is essential that the preparative separation period be set to include the peak top of the target component.

Upon starting the delay data acquisition operation under the preparative separation/fractionation conditions and LC analysis conditions determined in the previously described manner, the controller 8 first executes preparative separation/fractionation of the target component in the standard sample. Specifically, the sampler 34 is shifted by the actuator 35 to the upper side of the vial 67 in which the standard sample is held. A predetermined amount of the standard sample is suctioned from the vial 67 by the measuring unit 33, with the high pressure valve 31 forming the flow channel indicated by the solid line in FIG. 1, and the suctioned standard sample is kept in the measuring syringe of the measuring unit 33. Thereafter, the high pressure valve 31 is switched to the flow channel indicated by the dotted line in FIG. 1, and the standard sample kept in the measuring syringe is injected into the sample loop 32 and kept therein. Next, the high pressure valve 31 is again switched to the flow channel indicated by the solid line in FIG. 1 at a predetermined timing, which introduces the standard sample kept in the sample loop 32 into the column 4 along the flow of the mobile phase.

The target component in the standard sample elutes from the column 4 over a retention time specific to the component, and passes through the detector 5. In the case that real-time production of a chromatogram is performed by the data processor 9 based on the detection signals from the detector 5, a peak of the target compound appears in the chromatogram as indicated by the dotted line in FIG. 2($a$). The controller 8 switches the dispenser valve 62 in a manner that the eluate arriving to the fraction collector 6 is discharged to the waste vessel 64 until the start of preparative separation, and during the preparative separation period, operates the actuator 65 and the dispenser valve 62 to separate the eluate into different vials 67 one after another for each fractionation time width w. In this example, as shown in FIG. 2 ($a$), it is possible to separate the eluate into seven vials during the set preparative separation period. Since the feed rate of the pump is constant and the fractionation time width w is uniform, the same amount of the eluate is sampled in each of the seven vials as shown in FIG. 2($b$). Meanwhile, as the concentration of the target component in the eluate changes with time, the concentration of the target component in the eluate sampled in the seven vials is not the same. Herein, the seven vials are referred to as vials (1), . . . , (7) in time order.

Given that a chromatogram at the tip end of the dispenser nozzle 63 of the fraction collector 6 is produced, when a peak of the target component appears as shown in FIG. 2($a$), the eluate in each of the seven vials (1) to (7) should contain the target component in the amount corresponding to a portion of the peak area divided by the fractionation time width w. As the chromatogram with the peak shown in FIG. 2($a$) is not actually produced, the amount (or concentration) of the target component in the eluate collected in the respective vials (1) to (7) is not known at this stage.

After completion of the above preparative separation of the target component, the controller 8 executes an LC analysis to determine the amount of the target component in the eluate collected in each of the vials. Based on the already identified positions of the seven vials having the collected eluate in the rack 66, the controller 8 controls the actuator 35 in the injector unit 3 to shift the sampler 34 to a position above each of the seven vials 67 so as to allow the sampler 34 to suction the eluate from each of these vials 67. Then, in the same manner as the above preparative separation/fractionation operation, the sampler 34 suctions the eluate and injects it into the mobile phase, and an LC analysis is subsequently performed. The LC analysis needs to be repeated seven times if all the collected eluates are to be LC analyzed. It is naturally possible to perform the LC analysis for all the collected eluates; however, as will be described later, since part of the results of the quantity determination may be sufficient for estimating the delay data, it is possible to stop the LC analysis of the eluate at the time when all the necessary data are obtained.

In the LC analysis on the eluate separated in one of the vials, the detection signals sequentially sent from the detector 5 are fed into the data processor 7. The chromatogram producing section 71 in the data processor 7 produces a chromatogram. Since the same kind of the target component is contained in the eluate in the different vials, a peak of the target component appears at almost the same retention time in the chromatograms of the eluates in the respective vials. The height and the area of the peak depend on the amount of the contained target component, and thus the chromatograms showing the results of the LC analysis on the eluates in the seven vials of (1) to (7) will be as shown in FIG. 2 ($c$).

In the data processor 9, the peak detector 72 detects a peak in each of the chromatograms. Peak detection may be performed by known methods. For example, a peak can be detected by determining the gradient of a curve of a peak along the time axis, setting a time point as a starting point of the peak when the gradient of an ascending curve exceeds a predetermined threshold value, and detecting a time point as an ending point of the peak when the gradient of the descending curve reaches a predetermined threshold value after the gradient of the curve begins decreasing. The peak detector 72 fixes the starting point and the ending point of the curve, and calculates the peak area as the peak data. Peak height may be used in place of the peak area. However, use of the peak area improves the accuracy of delay data estimation because the peak area can absorb the variation in the reproducibility of the peak spread.

The eluate separated in one of the seven vials contains the maximum amount of the target component as long as the timing when the target component reaches the dispenser nozzle 63 is not substantially different from the preset preparative separation period at the time of the preparative separation. Namely, it is considered that the one eluate is fractionated in the time period corresponding to the peak top of the target component in the chromatogram. Based on this consideration, the delay estimator 73 extracts the peak area of the fraction having the maximum peak area and also extracts the peak areas of the previous and succeeding fractions on the time axis. In the example shown in FIG. 2($c$), the extracted peak areas are A1, A2, and A3 corresponding to the respective vials (2) to (4), including the peak area A2 of the fraction in the vial (3) which is the maximum area, and its previous and succeeding peak areas on the time axis.

The above-described extraction procedure indicates that, if the fraction including the maximum peak area is confirmed and the peak areas thereof and of its previous and succeeding fractions are determined, peak area data of the other fractions are not necessary. For example, in the case that an LC analysis and peak waveform processing are performed on the eluate in each vial along the time axis, since all the necessary data have been obtained at the time when the LC analysis and the peak waveform processing on the vial (4) are finished, the LC analysis and the peak waveform processing on the vial (5) and subsequent vials can be omitted. This, however, is for cases where three peak areas of the fraction having the maximum peak area and its previous and succeeding fractions on the time axis are used for estimating the delay data. In the case that peak area data of a larger number of fractions are used to improve the accuracy of the estimation, the number of the omittable LC analysis and peak waveform processing is naturally reduced.

The delay estimator 73 estimates the delay volume based on the extracted peak areas A1, A2, and A3. This process is explained by the following simple example, in which a center value of the fractionation time width w of the fraction having the maximum peak area is T2, a center value of the fractionation time width w of the immediately previous fraction is T1, a center value of the fractionation time width w of the immediately succeeding fraction is T3, and further the time of the peak top of the peak of the target component in the chromatogram based on detection signals obtained from the detector is T0. Then, the following equations are satisfied.

$$T1=T2-w, T3=T2+w \quad (1)$$

Given that the waveform of the peak is symmetrical to the vertical line passing the peak top, the position of the peak top can be estimated based on the ratios of the peak area of the center fraction including the peak top to the peak areas of the both sides of the fractions. Elution time Tt of the target component at the peak top at the tip end of the dispenser nozzle 63 is estimated by the following equation.

$$Tt=(-A1 \cdot T1+A2 \cdot T2+A3 \cdot T3)/(A1+A2+A3) \quad (2)$$

Substitution of equations (1) in equation (2) results in the following equation.

$$Tt=T2+(A3-A1) \cdot w/(A1+A2+A3) \quad (3)$$

As the T2 and w are obtainable from the set preparative separation/fractionation conditions, and the A1, A2 and A3 are obtainable by the above calculation, the elution time Tt of the target component at the peak top can be estimated by equation (3). When the feed rate of the pump during preparative separation is set as Ft, delay volume Vd satisfies the following equation.

$$Vd=(Tt-T0) \cdot Ft \quad (4)$$

As the T0 is obtainable from the chromatogram actually measured in the preparative separation operation, the delay volume Vd can be calculated by equation (4).

The delay estimator 73 performs the above calculation processing to give the delay volume Vd, and stores the delay volume Vd in a memory (not shown). Since the delay volume Vd is determined by the structural elements such as a piping which connects the detector 5 with the fraction collector 6, and the flow channel and the dispenser valve 62 installed in the nozzle head 61, the delay volume Vd, once obtained, does not change unless replacement of the piping or the like is performed. Therefore, the delay data acquisition operation as described earlier does not need to be frequently performed, and generally may be performed in an early phase after setting the system or after changing the structural elements such as the piping.

In actually performing the LC analysis, the feed rate of the pump is included in the analysis conditions. Therefore, based on the feed rate F of the pump set as the LC analysis condition and the delay volume Vd stored in the memory, the delay time Is for the feed rate of the pump is calculated by the following equation: Ts=Vd/F. Preparative separation of the target component may be initiated at a timing lagging by the delay time Ts behind the timing at which the component to be separated passes through the detector 5. The preparative LC system according to the present embodiment can determine the delay time Ts more accurately than conventional systems, and thus it can more precisely fractionate/separate the target component contained in the samples into the target vials. In the preparative separation of a plurality of components contained in a sample, preparative separation of each component may be performed at a timing lagging by the delay time Ts behind the timing at which each of the components is detected.

In the above embodiment, a peak top-appearing time is estimated based on the peak areas in the three consecutive fractions, with the middle one having the peak top. It is possible to increase the accuracy of the estimation by using the peak areas in four or more fractions.

There are two possible methods for controlling sampling of the eluate into a predetermined vial in the fraction controller 6. One method includes shifting the dispenser nozzle 63 to a position above a predetermined vial while the dispenser valve 62 is maintained on the dispenser channel side (or originally without having any dispenser valve 62), thereby starting the preparative separation, while the other method includes originally setting the dispenser nozzle 63 at a position above a predetermined vial with the dispenser valve 62 maintained at the waste channel side and then shifting the dispenser valve 62 to the dispenser channel side, thereby initiating the preparative separation. These two methods have a gap in the delay volume corresponding to the volume of the flow channel in the dispenser valve 62 and the inner volume of the dispenser nozzle 63. For this reason, the delay time differs depending on which of the preparative separation controls is chosen, and thus it is preferable to previously obtain appropriate delay volumes depending on the choice. In the case that both methods are available for controlling the preparative separation, the delay volume is preferably obtained for each of the two methods.

Figure 3:
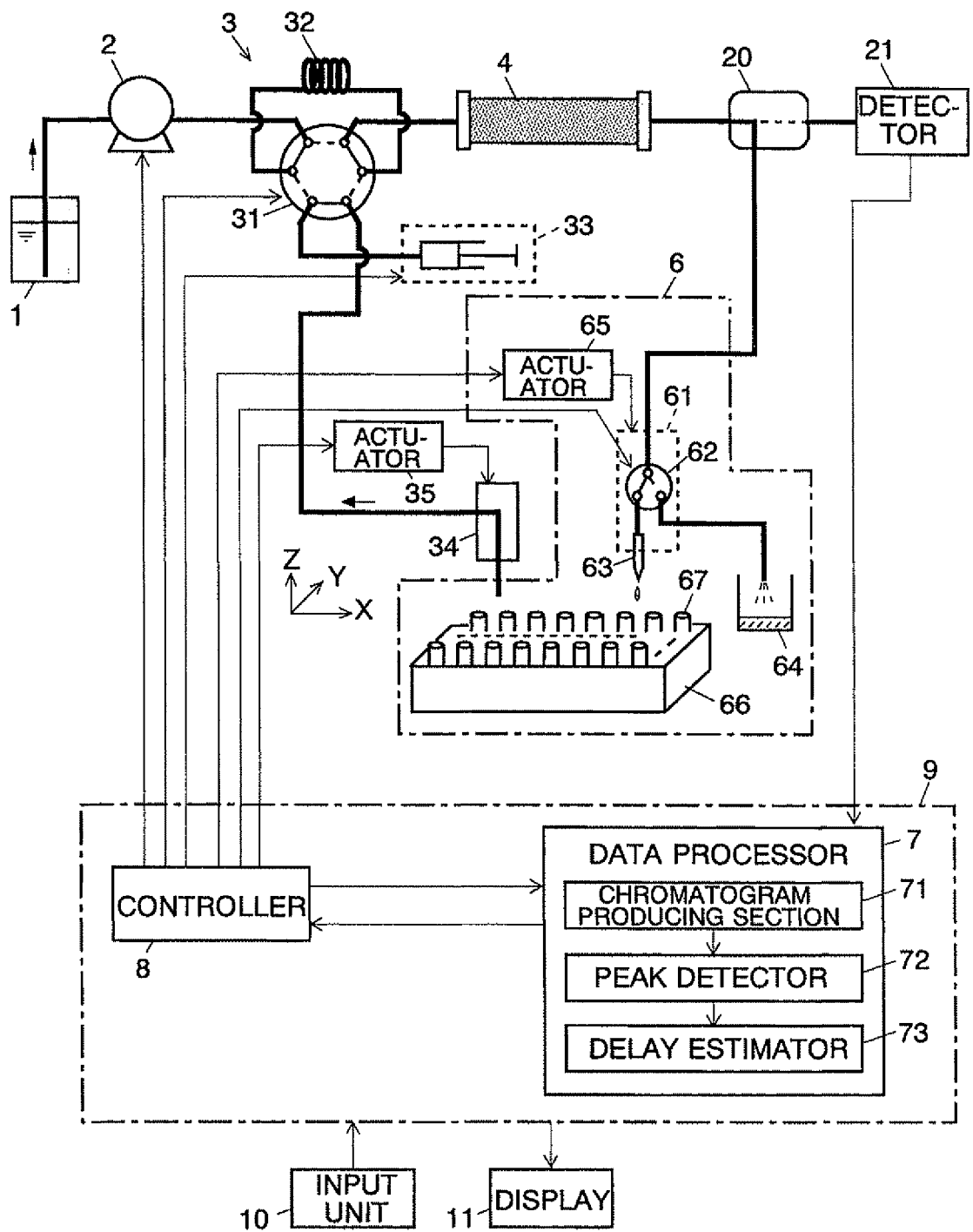
FIG. 3 is a configuration diagram showing main parts of the preparative LC system according to another embodiment.

The above embodiment employs a structure for cases where the detector 5 does not consume the eluate while detecting the sample component in the eluate. The present invention may also be employed in the case of using a detector consuming the eluate while detecting the sample component in the eluate. Typical examples of such a detector include mass analyzers and evaporative lightscattering detectors (ELSD). FIG. 3 shows one example of the structure in such cases.

In FIG. 3, the same structural elements as those in the example shown in FIG. 1 are marked with the same numerical symbols. In the preparative LC system, an eluate from the column 4 is introduced into the splitter 20, whereby a small portion of the eluate is branched to be introduced to a detector 21 such as a mass analyzer while the remaining, larger portion is sent to a fraction collector. The delay volume of this case is different from that in the example of FIG. 1 in that the delay volume is an apparent volume corresponding to the time period from when a component in the portion of the eluate branched by the splitter 20 reaches to and is detected by the detector 21 to when the same component reaches to the tip end 63 of the dispenser nozzle 63 of the fraction collector 6.

In the case of the preparative LC system shown in FIG. 3, the delay volume (the apparent volume) can be basically obtained by the same procedure as that in the above embodiment, and the delay time can be determined based on the delay volume so as to control the timing of the preparative separation. Meanwhile, in the example shown in FIG. 3, different split ratios at the splitter 20, even with the same feed rate of the pump, give different peak positions in the chromatogram, which affects the estimation of the delay volume. Split methods with the splitter 20 may be roughly divided into active methods and passive methods. The split ratio is highly stable in the active methods while the split ratio relatively tends to change in the passive methods. In the case that the split ratio easily changes, it is preferable to obtain the newest possible delay volume by performing the delay data acquisition operation as frequently as possible.

It should be noted that, other than those described thus far, any modification, adjustment, or addition appropriately made within the spirit of the present invention is also covered by the claims of the present patent application.

The invention claimed is:

1. A preparative liquid chromatograph (LC) system comprising:
an LC unit including a column for isolating a component in a sample and a detector for detecting the component in an eluate from the column;
a fraction collector for fractionating the eluate and separating each fraction of the eluate in individual containers;
a preparative separation execution controller for controlling the LC unit and the fraction collector to separate a single target component in a predetermined sample into a plurality of individual containers per a predetermined fractionation time;
an individual LC execution controller for controlling the LC unit to perform an LC analysis and obtain a chromatogram individually on the single target component separated in each of the plurality of containers;
a peak data calculator for deriving a peak data from a single component suctioned from different containers, corresponding to the amount of the single target component on each of the chromatograms; and
a calculation processor for estimating delay data on a delay from detection of a component in the eluate with the detector to separation of the component with the fraction collector, by using at least a peak data corresponding to a maximum amount of the single target component and its previous and succeeding peak data on a time axis obtained by the peak data calculator.

2. The preparative liquid chromatograph system according to claim 1, wherein the calculation processor estimates a delay volume of the eluate flowing in the period from detection of a component in the eluate with the detector to preparative separation of the component with the fraction collector, based on the plurality of the peak data, an amount of mobile phase flowing during the preparative separation conducted by the preparative separation execution controller, a peak position of the single target component in the chromatogram during the preparative separation, and a position of the container at which the peak data corresponding to the maximum amount is obtained or time data of when the preparative separation to this container is executed.

3. The preparative liquid chromatograph system according to claim 1, wherein the peak data is a peak area.

4. The preparative liquid chromatograph system according to claim 1, wherein: the calculation processor stores the estimated delay data; and the preparative separation execution controller controls, upon preparative separation of a given component in the sample, the timing of the preparative separation of the component by using the delay data.

5. The preparative liquid chromatograph system according to claim 1, further comprising a sample introduction means for selecting each portion of the eluate separated in each of the plurality of containers and for sequentially subjecting the selected portion of the eluate to an LC analysis.

6. The preparative liquid chromatograph system according to claim 2, wherein the peak data is a peak area.

7. The preparative liquid chromatograph system according to claim 2, wherein: the calculation processor stores the estimated delay data; and the preparative separation execution controller controls, upon preparative separation of a given component in the sample, the timing of the preparative separation of the component by using the delay data.

8. The preparative liquid chromatograph system according to claim 3, wherein: the calculation processor stores the estimated delay data; and the preparative separation execution controller controls, upon preparative separation of a given component in the sample, the timing of the preparative separation of the component by using the delay data.

9. The preparative liquid chromatograph system according to claim 6, wherein: the calculation processor stores the estimated delay data; and the preparative separation execution controller controls, upon preparative separation of a given component in the sample, the timing of the preparative separation of the component by using the delay data.

10. The preparative liquid chromatograph system according to claim 2, further comprising a sample introduction means for selecting each portion of the eluate separated in each of the plurality of containers and for sequentially subjecting the selected portion of the eluate to an LC analysis.

11. The preparative liquid chromatograph system according to claim 3, further comprising a sample introduction means for selecting each portion of the eluate separated in each of the plurality of containers and for sequentially subjecting the selected portion of the eluate to an LC analysis.

12. The preparative liquid chromatograph system according to claim 4, further comprising a sample introduction means for selecting each portion of the eluate separated in each of the plurality of containers and for sequentially subjecting the selected portion of the eluate to an LC analysis.

13. The preparative liquid chromatograph system according to claim 6, further comprising a sample introduction means for selecting each portion of the eluate separated in each of the plurality of containers and for sequentially subjecting the selected portion of the eluate to an LC analysis.

14. The preparative liquid chromatograph system according to claim 7, further comprising a sample introduction means for selecting each portion of the eluate separated in each of the plurality of containers and for sequentially subjecting the selected portion of the eluate to an LC analysis.

15. The preparative liquid chromatograph system according to claim 8, further comprising a sample introduction means for selecting each portion of the eluate separated in each of the plurality of containers and for sequentially subjecting the selected portion of the eluate to an LC analysis.

16. The preparative liquid chromatograph system according to claim 9, further comprising a sample introduction means for selecting each portion of the eluate separated in each of the plurality of containers and for sequentially subjecting the selected portion of the eluate to an LC analysis.

* * * * *